(12) United States Patent
Hedén et al.

(10) Patent No.: US 6,923,798 B2
(45) Date of Patent: Aug. 2, 2005

(54) MECHANICAL TAPE FASTENING SYSTEM FOR DISPOSABLE ABSORBENT ARTICLES

(75) Inventors: Anna Hedén, Vallda (SE); Robert Kling, Skene (SE); Monica Forgar, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/044,904

(22) Filed: Jan. 15, 2002

(65) Prior Publication Data

US 2002/0099352 A1 Jul. 25, 2002

Related U.S. Application Data

(60) Provisional application No. 60/262,657, filed on Jan. 22, 2001.

(51) Int. Cl.[7] .......................... A61F 13/15; A61F 13/20
(52) U.S. Cl. ...................................... 604/391; 604/389
(58) Field of Search .................... 604/385.11, 389–397, 604/385.13; 24/442–452

(56) References Cited

U.S. PATENT DOCUMENTS

| | | | |
|---|---|---|---|
| 3,554,195 A | | 1/1971 | Murdoch |
| 3,642,001 A | * | 2/1972 | Sabee .......................... 604/390 |
| 3,776,234 A | * | 12/1973 | Hoey .......................... 604/390 |
| 3,867,940 A | | 2/1975 | Mesek et al. |
| 4,100,921 A | * | 7/1978 | Schaar ........................ 604/390 |
| 4,576,598 A | | 3/1986 | Tritsch |
| 5,019,065 A | * | 5/1991 | Scripps .................. 604/385.21 |
| 5,019,073 A | | 5/1991 | Roessler et al. |
| 5,024,672 A | | 6/1991 | Widlund |
| 5,108,384 A | * | 4/1992 | Goulait ........................ 604/390 |
| 5,549,591 A | * | 8/1996 | Landvogt ..................... 604/389 |
| 5,830,206 A | * | 11/1998 | Larsson ....................... 604/390 |
| 5,961,761 A | * | 10/1999 | Heindel et al. ............. 156/163 |
| 5,968,030 A | * | 10/1999 | Shimizu et al. ............. 604/390 |
| 6,142,986 A | | 11/2000 | Lord et al. |
| 6,494,873 B2 | * | 12/2002 | Karlsson et al. ............ 604/392 |
| 6,526,631 B1 | * | 3/2003 | Alberg et al. ................. 24/306 |
| 6,648,871 B2 | * | 11/2003 | Kusibojoska et al. ....... 604/392 |

FOREIGN PATENT DOCUMENTS

| | | |
|---|---|---|
| EP | 0324578 | 7/1989 |
| EP | 0520087 A1 | 12/1992 |
| WO | 95/05140 | 2/1995 |
| WO | 98/22069 | 5/1998 |
| WO | 00/27329 | 5/2000 |

* cited by examiner

Primary Examiner—Karin Reichle
(74) Attorney, Agent, or Firm—Burns, Doane, Swecker & Mathis, LLP

(57) ABSTRACT

A disposable absorbent article includes first and second end portions, an intermediate crotch portion, and mechanical tape fasteners detachably interconnectable with at least one fastening parts disposed on the outer layer of the first end portion during a position of use. The tape fasteners are arranged on and joined to the inner layer of the second end portion via a producer's bonding face. A user's bonding face is arranged on an opposite user's end part of the tape fastener. Each tape fastener has an odd number of folds in a storage position. Producer's and user's bonding faces are turned towards the inner layer, the user end parts of the fasteners face one another, and the individual fold parts are joined to respective at least one other fold parts by means of a breakable bond in the storage position. The bond is breakable in order to establish the position of use.

19 Claims, 6 Drawing Sheets

MECHANICAL TAPE FASTENING SYSTEM FOR DISPOSABLE ABSORBENT ARTICLES

This application claims the benefit of U.S. Provisional Application No. 60/262,657 entitled MECHANICAL TAPE FASTENING SYSTEM FOR DISPOSABLE ABSORBENT ARTICLES and filed on 22 Jan. 2001, the entire content of which is hereby incorporated by reference.

TECHNICAL FIELD

The present invention concerns a disposable absorbent article, such as an baby diaper, an incontinence diaper or the like, comprising a first end portion and a second end portion, which portions are intended completely or partly to enclose the user's waist area during use of the article, and an intermediate crotch portion, said portions comprising an inner layer, which is turned towards the user during use and is liquid-permeable at least in the crotch portion opposite the user's genitals, a liquid-impermeable outer layer, and an absorbent body disposed between said outer and inner layer, The article is formed in the area of the second end portion with mechanical tape fasteners intended, upon application of the article, to be detachably interconnected with one or several fastening parts disposed on the outer layer of the first end portion and being complementary to said tape fasteners.

BACKGROUND ART

Various types of fasteners have been used for attaching disposable absorbent articles, e.g., baby diapers, incontinence diapers or the like, around the user's waist. Exemplary fasteners are adhesive tape fasteners and mechanical tape fasteners. Adhesive fastener systems allowing tape ends to be repeatedly fastened, unfastened and re-fastened have been available on the market since the beginning of the 1980s. One adhesive tape fastener system of this type is described in U.S. Pat. No. 5,024,672.

Analogous to adhesive tape fastener systems and adhesive tape fasteners are mechanical tape fastener systems and mechanical tape fasteners to define fastener systems and fasteners. In such mechanical systems and fasteners, the bond is effected not by adhesive means but by means of mechanical interlocking between hooks disposed on one of the parts of a fastening known as a hook-and-loop fastener and loops, apertures or fibre filaments disposed on the other hook-and-loop fastener part.

In most respects, modern adhesive tape fastener systems function satisfactorily. However, a serious problem is the deteriorated quality of the adhesion, should, e.g., talcum powder or baby oil be spilled onto the pressure-sensitive adhesive substance or onto the bonding face to which the tape is to be attached. This problem may be removed by using mechanical tape fastener systems. In addition, consumers want disposable absorbent articles that are soft to the touch and have a textile-like appearance as opposed to the plastic films of which outer layers of disposable absorbent articles were predominantly formed. Hitherto, mechanical tape fastener systems have been too expensive to compete with adhesive tape fastener systems. In recent years novel mechanical tape fastener systems have been developed that are more price-competitive. This fact in conjunction with the increasing use of textile-like outer layers and elimination of the problems caused by spillage on the bonding faces, has contributed to manufacturers of disposable absorbent articles using mechanical tape fastener systems more.

By applying mechanical tape fasteners on both sides of, e.g., the rear end portion of a diaper, and providing a complementary bonding face on the external face of the opposite end of the diaper in a manner corresponding to that described in U.S. Pat. No. 5,024,672, the problem of fastening of the diaper as it is being put on, unfastening it and refastening thereof is solved. Such a mechanical tape fastener system is also described in, e.g., EP-A1-0324578. This publication also touches on the problem involved in sealing a used diaper such that it forms a closed package for reliable enclosure of feces inside the diaper, and the publication describes one means of solving this problem.

The latter publication mentions the problem arising because the mechanical tape fastener may unintentionally hook onto parts of the diaper before attachment to the intended bonding face has been made.

Over the years, the permanent anchorage of tape fasteners has been subject to much development, and many suggested solutions have been presented in the patent literature. This is also true of the problem of protecting the bonding face of the tape fasteners from unintentionally adhering where not wanted before the diaper is put on. The tape fasteners, which are anchored to the article by the producer in the process of the manufacture of the article, are exposed to considerable stress as the diaper is being put on and the forces arising in connection therewith are absorbed by the point of anchorage. If the tape fastener is attached to the external layer of the article only, there is a risk that this layer be torn as the article is being put on. This problem is discussed in U.S. Pat. No. 3,867,940, and the solution suggested therein is to reinforce the external layer in the area of the point of anchorage.

The solution most predominantly found on the market and also in the patent literature is the use of the so-called Y-tape, which comprises two branches that are applied about the edge portion of the diaper, with one branch on the external layer and the other on the inner layer, thus making use of the inherent strength of the inner as well as of the external layer. The above publication EP-A1-0324578 and WO 95/05140, e.g., disclose a Y-tape designed for mechanical tape fasteners.

One disadvantage inherent in Y-tapes is that they have to be attached during manufacturing on both sides of an edge portion of a disposable absorbent article, such as a diaper. The manufacturing utilizes a web travelling at a very high speed, a feature that makes the application of Y-tapes very complex. A further disadvantage is that the position of tape fasteners, applied around the edge portion of the rapidly advancing web of articles, may lead to serious drawbacks, both as regards the freedom of changing the manufacturing process and the freedom of changing the article itself.

Another prior-art solution is the so-called Z-folded tape, which is anchored permanently to the external face of the outer layer of the article. A Z-folded tape is shown, e.g., in U.S. Pat. No. 4,576,598. A drawback inherent in Z-folded tapes is that they are attached to the external face of the outer layer of, e.g., a diaper. The result is that the Z-tape, once attached, is unprotected during the subsequent processing steps, which usually include cross-cutting, cross-folding and insertion in a bag. To some extent this is applicable also to diapers comprising Y-tapes.

In the storage condition of the article, i.e., before it is used, adhesive and hook-on fastening parts on the tape fasteners should be safely covered in order to prevent unintentional hook-on or adhesion that makes handling of the article more difficult as the latter is being put on. Hitherto, this problem usually has been solved by ensuring that in the storage condition of the tape fasteners, adhesive parts on the fasteners, including mechanical tape fasteners, abut against release-agent coated plies of material. A solution of this kind is described for instance in the above mentioned EP-A1-0 324 578. Release-agent coatings are, however, comparatively expensive while at the same time they often require the provision of an additional layer of material in the tape fastener, which makes the design of the latter more complex. When mechanical tape fastener systems are used, it is conceivable to arrange for the mechanical bonding faces of the tape fastener, in the storage condition of the latter, to abut against and be mechanically interconnected with a part of a hook-and-loop fastener that is complementary to said bonding face. If a safe interconnecting bond is wanted, a solution of this kind requires the provision of complementary bonding faces for all mechanical fasteners of the article, with resulting increased material costs for and a more complex manufacture of said article.

SUMMARY OF PREFERED EMBODIMENTS

By means of the present invention, the above problems found in absorbent articles of the kind defined in the introduction have been eliminated.

For this purpose, the article in accordance with the invention comprises at least two of said tape fasteners, which are arranged on the inner layer of the article at opposite side portions of said second end portion, wherein the tape fasteners have one longitudinal and one transversal extension, wherein said tape fasteners are permanently joined to the inner layer of the article by means of a producer's bonding face arranged on a first end part of the tape fasteners, wherein a user's bonding face is arranged on the opposite second end part of the fasteners, the user's end part, wherein prior to use of the article, the tape fasteners are arranged in a folded storage condition, each one of said tape fasteners being formed with an odd number of folds and the bonding faces of both said producer's bonding face and said user's bonding face being turned towards the inner layer of the article, wherein the user's end parts of two opposite tape fasteners face one another in said storage condition and wherein in the storage condition of said article individual fold parts are joined to at least one of the other fold parts by means of a bond, preferably in the form of thermal or ultrasonic welds, said bond being breakable in order to establish the position of use of said tape fasteners.

Because the mechanical tape fastener is attached to the inner face of the inner layer of the article, the manufacturing process may be performed in a simpler and more reliable manner than in the case of the prior-art solutions involving Y-tapes. All folding steps with regard to the mechanical tape fasteners for the article in accordance with the present invention may be performed at a considerable lower speed than at the high web velocities found in modern machines for rational and competitive production of disposable absorbent articles, such as baby diapers. Anchorage of the fully folded mechanical tape fastener in accordance with the present invention onto the web of articles travelling at a high speed may be effected in a more controlled way than when Y-tapes are used, which need to be folded about the edge portion of individual articles. To attach the mechanical tape fasteners to the article in accordance with the teachings of the present invention only the producer's bonding face need to be applied against the inner layer and be connected to that layer. From a production point of view, such application is simpler and offers a larger degree of freedom as concerns production changes and replacements of the materials of which the article is constructed.

By the expression "breakable bond(s)" as used herein is to be understood bonds that do not require supplementary materials such as release coatings or an additional bonding zone designed solely for the storage condition of the tape fastener. Preferably, the bonds are in the form of thermally or ultrasonically produced welds.

In their condition of storage, the tape fasteners preferably are arranged in their entirety on the inner layer, with the laterally outermost end edges of the tape fasteners being located interiorly of the lateral edges of said lateral portions. In this manner, the tape fasteners are well protected during the subsequent processing steps, particularly in the case of the conventional hourglass-shaped disposable absorbent articles discussed herein, i.e. baby diaper, adults' diapers and the like, wherein the tape fasteners are arranged on lateral portions that are folded inwards prior to cross-cutting, cross-folding and insertion into packages.

In another suitable embodiment of the invention, in the condition of storage of the article, the mechanical tape fasteners comprise one fold only and in that the latter forms the laterally outermost end edge of the tape fastener in said storage condition, that the tape fasteners comprise a middle part, which by means of said breakable bond is connected to the first end part and which covers the latter, and in that when the user's bonding face is in said folded storage condition, the opposite end part is located laterally interiorly of the first end part.

Additional preferred embodiments will appear from the appended claims.

BRIEF DESCRIPTION OF DRAWINGS

The invention will be described in closer detail in the following with reference to the accompanying drawings, wherein.

DETAILED DESCRIPTION

Figure 1:
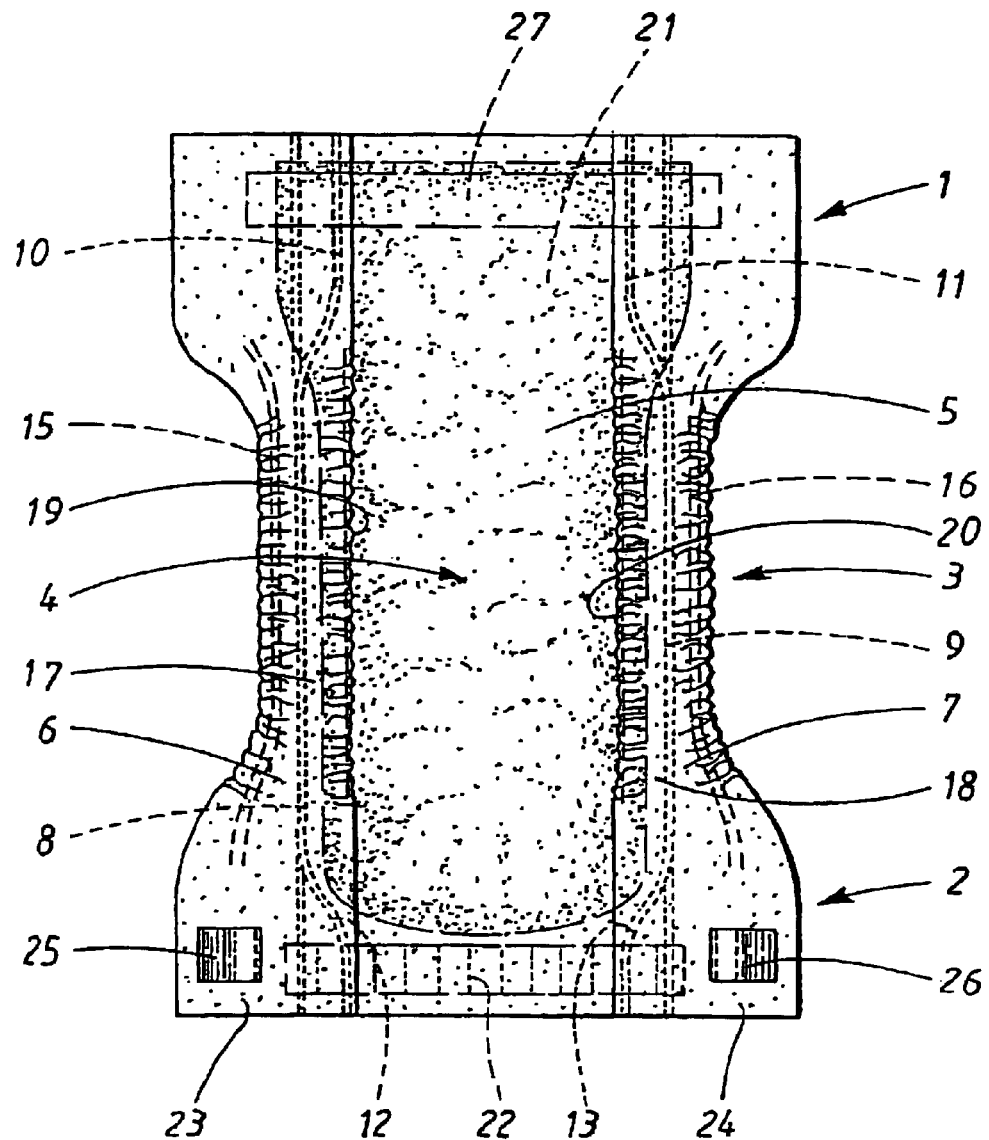
FIG. 1 shows a baby diaper and a flat, extended position and as seen from the inside towards the inner layer of the diaper.

The baby diaper illustrated in the drawing is hourglass-shaped, including a first end portion 1, a second end portion 2, and an intermediate crotch portion 3. The diaper comprises an inner layer 4 consisting of a longitudinally extending middle portion 5, the central area of which is liquid-permeable and which consists of, e.g., a fiber cloth, a so-called non-woven fabric, and two longitudinally extending lateral edge portions 6, 7, which preferably are liquid-impermeable or hydrophobic. The middle portion 5 is connected to the lateral edge portions 6, 7 by means of interconnecting lines 8, 9 and 10, 11, 12; 13, said interconnecting lines preferably being in the form of ultrasonic welds. The lateral portions 6, 7 may consist of a non-woven fabric that has been treated to make hydrophobic, or of some other liquid-impermeable material known to the expert. The inner layer comprised of said portions is joined at least along its lateral and end edges to an external layer 14, which in the present case is formed in one piece from a liquid-impermeable material, such as a laminated product of polyethylene and a thin outer layer of a fiber cloth.

Along the edges of the crotch portion 3, the diaper is provided with leg-abutting elastic means 15, 16. The lateral portions 6, 7 overlap the middle portion somewhat laterally, forming inner barriers 17, 18 serving to prevent urine and feces from spreading sideways in the diaper in the direction towards the diaper edges. The barriers 17, 18 are provided at their inner edges with pre-stressed elastic bands or threads 19, 20, which extend essentially along the crotch area of the diaper and which are arranged, when the diaper is in use, to make the barriers stand up from the inner layer. In the end portions of the diaper, the barriers are kept in a position of abutment against the middle portion 5 by means of the interconnecting lines 10–13. An absorbent body 21 is enclosed between the outer layer 14 and the inner layer 4. In accordance with the shown embodiment, the absorbent body 21 widens somewhat in the area of the first end portion 1, the front portion, and has a softly rounded configuration in the opposite end portion, the rear portion 2 of the diaper. The absorbent body 21 could consist of, e.g., cellulose fluff having mixed thereinto high absorbent materials in the form of particles or fibers.

At the rear portion 2 of the diaper, a pre-stressed elastic waistband 22 is provided between the outer and inner diaper layers.

Figure 2:
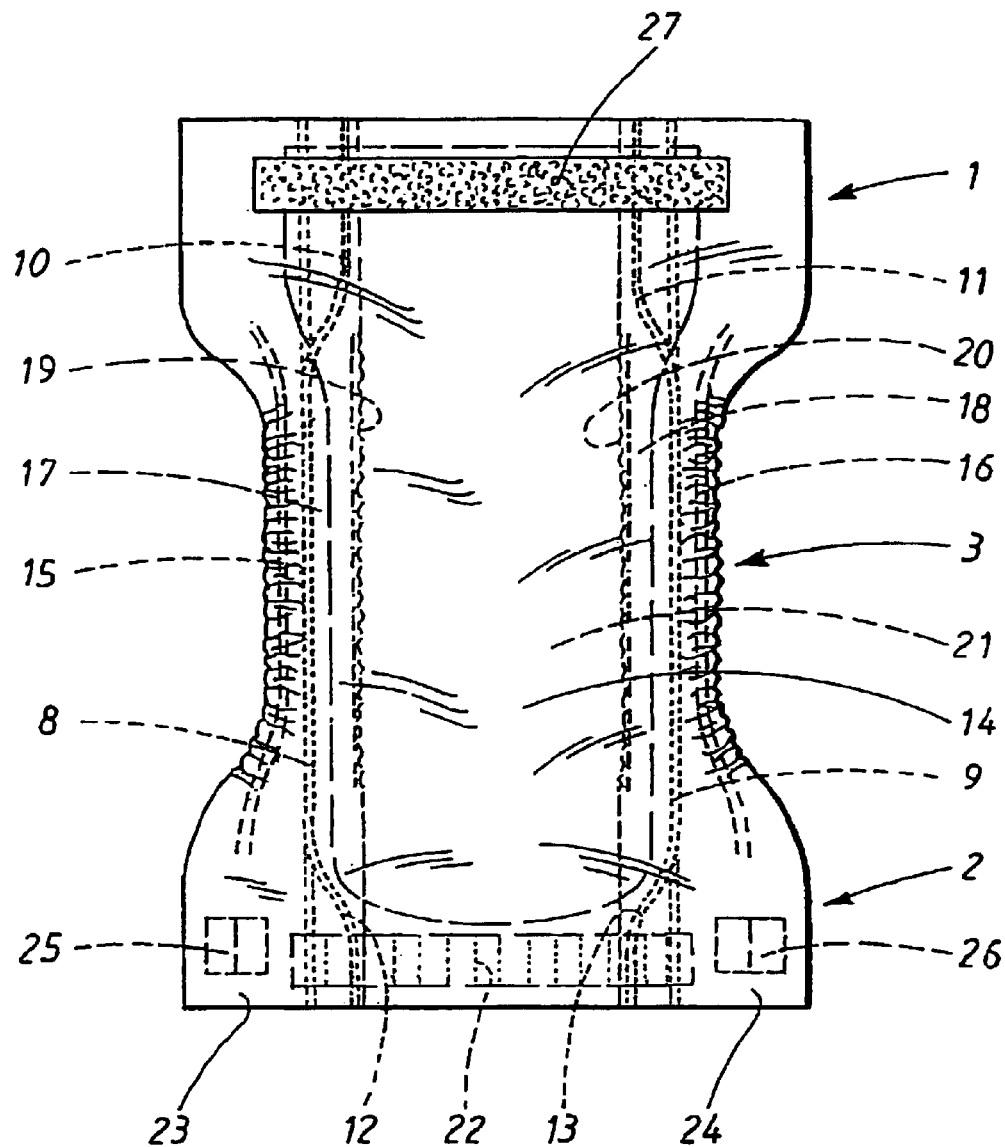
FIG. 2 shows the baby diaper of FIG. 1 in a flat, extended position as seen from the outside towards the outer layer of the diaper.

At the two opposite lateral portions 23, 24, viz. the corner portions of the rear diaper portion 2, the diaper is provided with mechanical tape fasteners 25, 26, which are permanently joined to the inner layer 4 by means of a producer's bonding face. At the opposite end portion 1 of the diaper, viz. the front portion, a bonding face, complementary to the mechanical tape fasteners, is arranged on the external face of the outer layer 14, as most clearly apparent from FIG. 2. This bonding face is formed by an elongate band 27, serving as one of the parts of a fastening of the kind known as a hook-and-loop fastener, the other part of which is formed by a user's bonding face on the tape fasteners as will be described in closer detail in the following. The material of the elongate band 27 is formed with apertures, loops or fiber filaments for co-operation with hooks formed on the tape fastener. Examples of suitable materials for the elongate band are described in EP-A1-0 324 578.

Figure 3:
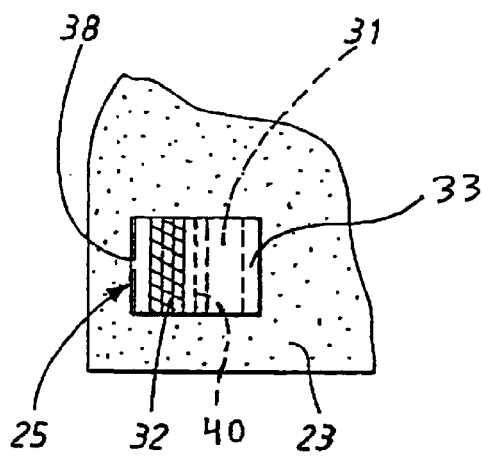
FIG. 3 is a view on an enlarged scale of a corner portion of the diaper of FIG. 1, showing a mechanical tape fastener in condition of storage attached to the inner layer of the diaper.
Figure 4:
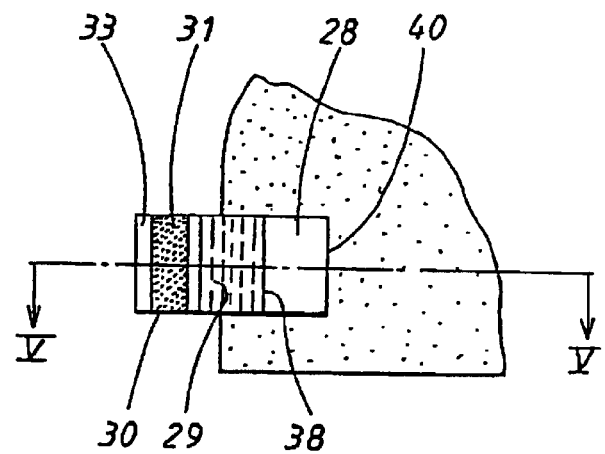
FIG. 4 is a view of the corner portion of FIG. 3, showing the tape fastener in the position of use.
Figure 7:
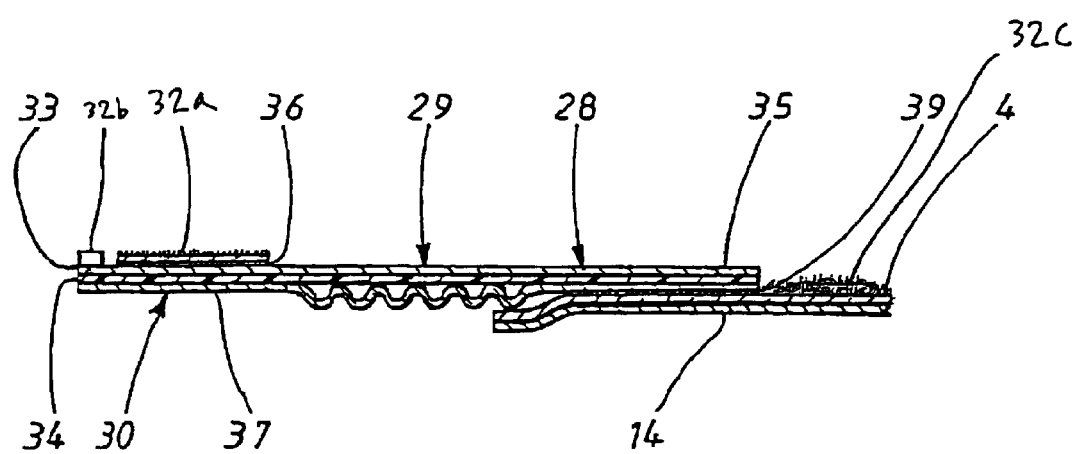
FIG. 7 is a sectional view according to an embodiment, shown on a larger scale.

FIG. 3 illustrates a mechanical tape fastener 25 as attached in its storage position to the inner layer of the corner portion 23. The tape fastener is prefabricated and is applied in folded condition, the single fold 38 forming the laterally outermost end edge of the tape fastener. Between the fold 38 or end edge and an edge 40, the fastener is formed with a producer's bonding face 28 (see FIG. 5) which is coated with an adhesive 39 for permanent anchorage of the tape fastener in the process of manufacture of the baby diaper. In accordance with the shown embodiment, the tape fastener comprises a support strip comprising three layers, which will be described in more detail with reference to FIG. 5. The support strip essentially has three subparts, which are most clearly apparent from FIGS. 4 and 5. One sub-part is formed by the producer's bonding part 28 that extends between the fold 38 and the edge 40. In addition, there is a middle part 29 and a distal part 30. One of the parts of a hook-and-loop fastener is applied on that latter part, said part being a strip formed with a users' bonding face 31 in the form of hooks or the like, said hooks projecting from the strip and, upon use of the hook-and-loop fastener as the diaper is being put on about the waist of the user, being anchored in the elongate band 27 that forms the other part of the hook-and-loop fastener. In one embodiment (FIG. 7), the inner layer 4 of the article comprises fibers 32c in which the hooks 32a of the user's bonding face 31 fasten to form a bond which is weaker relative to the bond of interconnection of the hook-and-loop fastener and the bond between the middle part 29 and the first end part. Examples of a mechanical tape-attachment part formed with hooks or the like to form said users' bonding face 31 are shown in EP-A1-0 324 578.

In its storage condition, the tape fastener 25 is folded as shown in FIG. 3. In this condition the middle part 29 is joined to the producer's part 28 by means of a bond in the form of thermal or ultrasonic welds. FIG. 3 shows this bond 32 in the form of a pattern of linear welds. The advantage of this type of bond is that no additional material in the form of glue or release-agent coatings and associated support strips are needed. In the storage condition, the users' bonding face 31 including the hooks and similar means thereon is protected by the support strip of the tape fastener and there is no risk for unintentional hook-on of the bonding face before the bond 32 is broken. The inner layer of a baby diaper usually has a textile-like open fibrous face to which the bonding face 31 of the mechanical tape fastener adheres somewhat, and in the storage condition, the bonding face 31 adheres weakly to the inner diaper layer at the corner portion 23. The outer edge portion 33 externally of the bonding face 31 could alternatively be provided with a pressure-sensitive bonding agent (32b in FIG. 7). The bonding agent serves both to bind the distal part of the tape fastener stronger to the inner layer of the diaper in the storage condition of the latter and to seal the used diaper such that a package is formed enclosing urine and feces inside the diaper.

Figure 5:
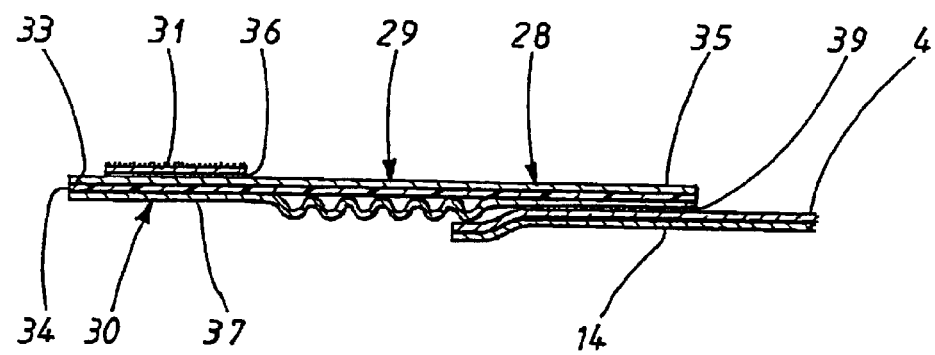
FIG. 5 is a sectional view along line V—V of FIG. 4, shown on a larger scale.

The support strip of the tape fastener 25 is a three-ply strip as shown in FIG. 5. An intermediate ply 34 in the form of an elastic film, which is elastically stretchable when exposed to stress in conjunction with the putting-on of the diaper and as the infant moves. Stress normally occurring in conjunction with the putting-on of the diaper is in the order to 200–2000 g, the stress being higher on the tape fastener that is secured the last compared with that on the tape fastener that is secured first. Stress load arising during use of the diaper as a result of the movements of the infant is in the order of 100–500 g, possibly somewhat higher in the case of chubby infants.

In accordance with the shown embodiment, a ply 35 of a non-woven fabric is laminated together with the elastic film. The non-woven ply follows the movements of the elastic film. The strip formed with the mechanical bonding face of the tape is joined to said non-woven ply 35 by means of a bonding agent 36. A ply 37 of a non-elastic fabric is attached to the opposite face of the elastic film 34. By non-elastic as used herein, is to be understood that the ply 37 does not stretch when subjected to the stress to which the tape fastener is exposed during use of the diaper. Along the producer's bonding part 28 and along the distal part, the non-elastic non-woven ply is joined to the elastic film, with the result that the elastic capacity of the latter is lost in these areas. In the middle part 29, however, the non-elastic non-woven ply is corrugated and joined to the elastic film at spaced-apart points only, as shown in FIG. 5. Consequently, the middle part of the tape fastener is elastically stretchable from the position of FIG. 5 to the completely extended position, wherein the corrugations of the non-elastic non-woven ply are completely straightened-out. FIG. 5 shows part pieces of the inner layer 4 and the external layer 14 of the diaper as well as a coat 39 of an adhesive coating, viz. the producer's bonding face, disposed between the tape fastener and the inner ply.

The bond 32 between the middle part 29 of the tape fastener and the producer's bonding part 28 should be of a magnitude ensuring reliable attachment of the mechanical tape fastener to the diaper in the folded tape-fastener position while at the same the bond should not be difficult to break for the person that is about to put on the diaper. Research has shown that the bond is too weak when forces below 0.2 N are sufficient to unfasten a strip having a width of 40 mm, whereas the bond is difficult to break, when forces above about 2.0 N are required to unfasten a strip having a width of 40 mm. Thus, the bond functions satisfactorily, when a force in the range of from 0.2 to 2.0 is required to break the bond on a strip having a width of 40 mm. Preferably, the required force to break the bond should range from 0.5 to 1.5 N for a strip having a width of 40 mm.

The measurement method for determination of the force necessary to break the bond will be described in the following example.

Testing method for measurement of lamination strength:

The object of this method is to determine the mean value of the force necessary to separate from one another two different sheets of a laminate. This method is applicable to laminates comprising two or several sheets that are joined together by gluing, thermo-bonding or welding.

Principle

Separate the sheets and attach the individual sheets in a tensile strength tester and hold the non-separate part in a manner ensuring that delamination takes place at an angle of 90°.

Test the material in the transverse and the machine directions.

Equipment:
Tensile strength tester
Printer with plotter function
Punching or cutting equipment
Preparation of Specimens:

Cut or punch specimens of 25×200 mm, five in the transverse direction and five in the machine direction. The strips should be evenly distributed over the entire specimen.

Condition the specimens for 4–48 hours at an air humidity level of 50±5% and at 23±2° C.

Wet specimens: Put the test strips in a sealable plastic bag. Pour deionized water into the bag and seal it. Leave it in a climate-controlled space for 4 hours. Do not wet more test strips at a time than can be delaminated within 30 minutes. In this manner, all test strips will have a "wet time" of between 4 and 4.5 hours.

Figure 6:
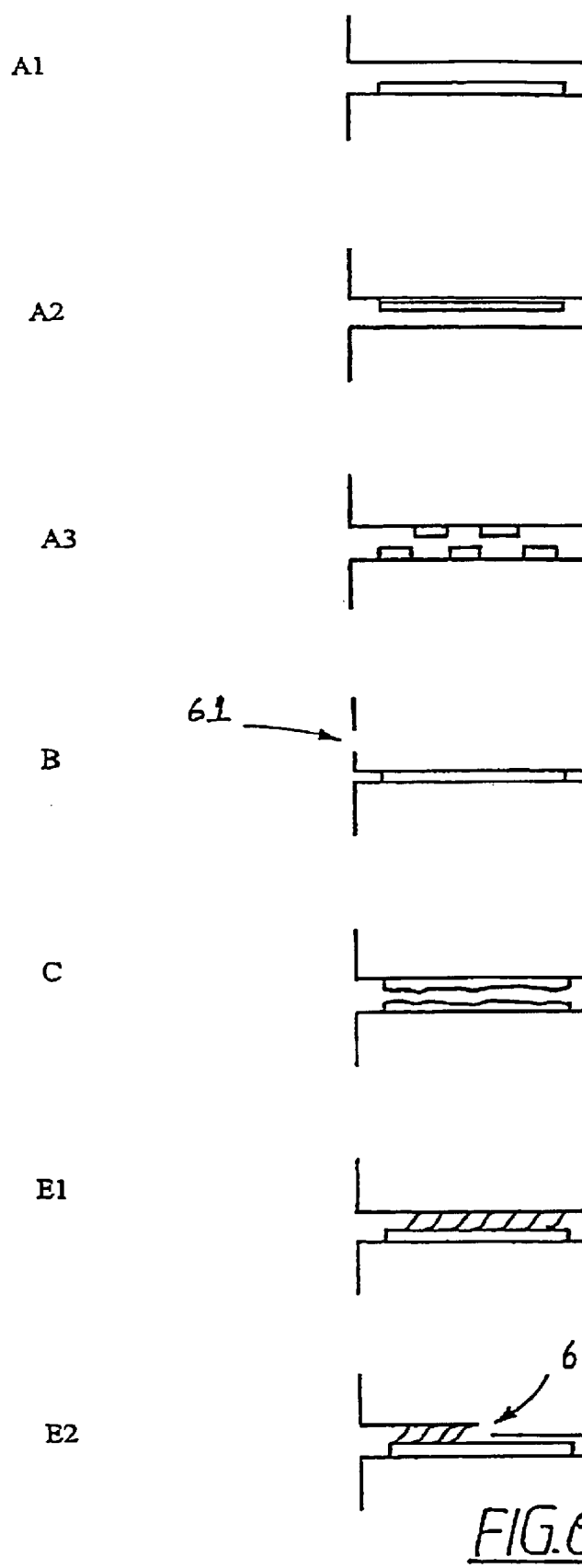
FIG. 6 is a schematic view of different types of bond ruptures obtained by means of a method of testing the strength required to break a bond in the tape fastener in the storage condition of the latter.

Procedure:
Prepare the tensile-strength tester in accordance with the apparatus instructions.
Length of clip 50 mm.
Pulling speed 300 mm/min.
Speed of paper 300 mm/min.
Calibrate the tensile-strength tester.
Separate the sheets at one end of the test strip.
Attach the edges in the clips.
Support the laminated part of the specimen with one hand, loosely and at right angles to the laminated part, during the testing process
Note the force during displacement of the draw-head over 250 mm, i.e., during delamination of a length of 125 mm.
In the case of glued laminates: Note when the delamination occurs and note the respective separation codes. Various separation codes and the corresponding separations are shown in FIG. 6. A1=Adhesion break, glue remains on carrier. A2=Adhesion break, glue transferred to the opposite material. A3=Alternative adhesion break. B=Rupture of material externally on bond. C=Defective cohesion, glue shattered. E1=Minor fiber rupture. E2=Rupture of material in bond.
Perform five acceptable tests in the cross-machine direction and five in the machine direction Calculate and Note the Results:
Calculate the mean force (N/25 mm) and the mean peak value (N/25 mm) of the movement of the draw-head from 10 mm to 210 mm.

The force for breaking the bond is proportional to the width of the strip. That is, such that a test result for 25 mm width can be directly transformed to the necessary force for a strip which is 40 mm in width by multiplying by 8/5.

The report is to include:
The number of test strips/specimens
Mean value of the mean delamination force in the transverse direction and in the machine direction
Mean value of maximum values
Mean value of minimum values
Standard deviation
Specification of Separation Code List (Example: 2 A1+3B)
Accuracy: 0.01 N
Reference: ASTM D 1876-72

The mechanical tape fastener 25, 26 in accordance with the present invention is attached in folded condition to the inner face of the inner layer 4. The manufacturing process may therefore be performed in a simpler and more reliable manner than in the case of prior art solutions, such as Y-tapes. As mentioned above, all folding steps with regard to the mechanical tape fasteners for the article, in accordance with the present invention may be performed at a considerable lower speed than at the high web velocities found in modern machines for rational and competitive production of disposable absorbent articles, such as baby diapers.

The manufacturing of the mechanical tape fasteners in accordance with the present invention can be performed at such a first, lower speed which is only about 5–30% of a second, higher speed at which the diapers are produced.

The process for manufacturing mechanical tape fasteners includes the following steps:

A. A carrier web, e.g., of a three-ply configuration as has been described in connection with the embodiment shown in FIG. 5, i.e. an intermediate ply in the form of an elastic film, a non-woven ply and a non-elastic ply of a non-woven, is supplied to a manufacturing line for the mechanical tape fasteners.

B. A longitudinal edge part of the carrier web is folded over itself.

C. The folded edge part is attached to the unfolded part by means of a weak, breakable bond, preferably in the form of thermal or ultrasonic welds. The bond can be in the form of a pattern of linear welds or spaced apart dots. The bonds can represent a part of a pattern or be randomly distributed.

D. In case two rows of carrier webs are formed out of the same base material the carrier web is divided.

E. Diaper user attachment means in the form of a web with projecting hooks, intended to form one part of a hook-and-loop fastener are joined to the unfolded parts.

F. Diaper manufacturer attachment means, in the form of glue are joined to the folded part of the carrier web so that both user and manufacturer attachment means are facing at the same direction.

G. Diaper fastening tabs are formed by cutting the tab carrier material perpendicular to the travelling direction.

H. The diaper fastening tabs, which have been formed at a first low speed, are accelerated from the first, low speed to a second, higher speed, corresponding to the manufacturing speed of the diapers.

I. The diaper fastening tabs are attached at said second, higher speed to the upward facing side of the diaper material web forming the inner layer of the diapers.

An attached diaper fastening tab is shown in FIG. 3. The outer edge portion 33 externally of the fastening part 31 could possibly be provided with a pressure sensitive adhesive (32b in FIG. 7) when the fastening part with hooks are fastened to the carrier web in step E above.

The invention is not limited to the examples described above but several modifications are possible within the scope of the appended claims.

The elastic tape fastener may comprise several folds when in its storage condition. This may be appropriate if longer tape fasteners are desired, e.g., when it is desirable to give the diaper itself a more narrow shape. It is essential, however, that the number of folds is an odd number to allow the tape fasteners to be attached permanently to the inner layer and by means of the mechanical tape bonding face be joined to the complementary bonding face on the outer face of the outer layer.

The tape fastener naturally need not be designed with three plies. The internal non-woven ply 35, for instance, may be dispensed with.

In addition, also the corrugated non-woven ply may be eliminated. One example of a suitable material of this kind is an elastic film marketed by TREDEGAR under the name FABRIFLEX 106D.

Figure 8:
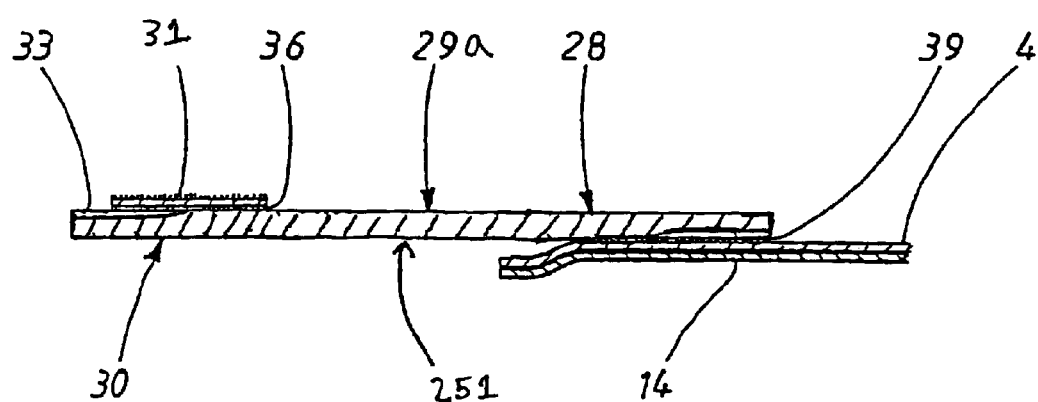
FIG. 8 is a sectional view according to an embodiment, shown on a larger scale.

The tape fastener need not either include an elastic part. A suitable non-elastic alternative (25' in FIG. 8)is a spunbond non-woven product having a weight per unit of 40–100 g/m2 marketed by PEGAS.

The above description has been made with reference to a baby diaper. However, the present invention also embraces adult diapers and other sanitary disposable absorbent articles that may be attached about the waist of the wearer, such as women's sanitary diapers. The width of the mechanical tape fastener may be in the order of 40 mm. If longer tape fasteners are desired, the width may be increased for more stability. The width of the tape fasteners should be in the range of 30 to 100 mm.

What is claimed is:

1. A disposable absorbent article, comprising:
a first end portion and a second end portion, which portions are intended at least partly to enclose a user's waist area during use of the article, and an intermediate crotch portion,
said portions comprising an inner layer, which inner layer is turned towards the user during use and which inner layer is liquid-permeable at least in the crotch portion adapted to be opposite the user's genitals, a liquid-impermeable outer layer, and an absorbent body disposed between said outer and inner layers;
said article including in the area of the second end portion at least two mechanical tape fasteners, the mechanical tape fasteners adapted to be, upon application of the article on the user, detachably interconnected with at least one fastening part disposed on the outer layer of the first end portion and being complementary to said mechanical tape fasteners, wherein the two mechanical tape fasteners are oppositely arranged on the inner layer of the article at opposite side portions of said second end portion, the two mechanical tape fasteners each have one longitudinal and one transverse extension, said mechanical tape fasteners are each permanently joined to the inner layer of the article by means of a producer's bonding face arranged on a first end part of each of the tape fasteners, a user's bonding face is arranged on an opposite second end part of each of the tape fasteners, and wherein prior to use of the article, the tape fasteners are arranged in a folded storage condition, each one of said tape fasteners being formed with only one fold and both said producer's bonding face and said user's bonding face being turned towards the inner layer of the article in the storage condition, the second end parts of the two tape fasteners extending toward one another in said storage condition and in the storage condition of said article, each of the tape fasteners includes a first fold part formed by the second end part that is joined to at least one other fold part formed by the first end part by means of a bond, said bond being breakable in order to interconnect the user's bonding face to said at least one fastening part upon application of the article, and wherein in their condition of storage, the tape fasteners are arranged in their entirety on the inner layer, with laterally outermost end edges of the tape fasteners formed by the respective said one folds being located interiorly of lateral edges of said opposite side portions;
wherein in said folded storage condition, in each of said tape fasteners the opposite second end part is located laterally interiorly of the first end part so as to cover the latter;
wherein each user's bonding face is in the form of hooks of a hook-and-loop fastener and the at least one complementary fastening part being formed with apertures, loops or fiber filaments for co-operation with the hooks; and
wherein the inner layer of the article comprises fibers to which the hooks of each user's bonding face fasten in the storage position to form a bond which is weaker relative to a bond formed by the interconnection of the hooks of each of the user's bonding faces and said at least one complementary fastener and said breakable bond between the second end part and the first end part in the storage position.

2. The article as claimed in claim 1, wherein an outermost end piece of the second end part of each of the mechanical tape fasteners is coated with a pressure-sensitive adhesive providing a weak adhesion force.

3. The article as claimed in claim 1, wherein each breakable bond is designed to ensure that a force in the range of 0.2 to 2N is required to break the bond when the mechanical tape fasteners have a transverse extension of 40 mm.

4. The article as claimed in claim 1, wherein each breakable bond is in the form of a pattern of points or lines, and the bond is breakable without damage to the tape fastener.

5. The article as claimed in claim 1, wherein the mechanical tape fasteners have a width of between 30 and 10 mm.

6. The article as claimed in claim 1, wherein each of the mechanical tape fasteners comprise at least one elastic part disposed between the first end part and the second end part, said elastic part arranged to stretch upon occurrence of load during use of the article.

7. The article as claimed in claim 1, wherein the mechanical tape fasteners do not stretch upon occurrence of load during use of the article.

8. The article as claimed in claim 1, wherein the article is a baby diaper or an incontinence diaper.

9. The article as claimed in claim 1, wherein each breakable bond is designed to ensure that a force in the range of 0.5 to 1.5N is required to break the bond when the mechanical tape fasteners have a transverse extension of 40 mm.

10. A disposable absorbent article, comprising:

a first end portion and a second end portion, which portions are intended at least partly to enclose a user's waist area during use of the article, and an intermediate crotch portion, said portions comprising an inner layer, which inner layer is turned towards the user during use and which inner layer is liquid-permeable at least in the crotch portion adapted to be opposite the user's genitals, a liquid-impermeable outer layer, and an absorbent body disposed between said outer and inner layers;

said article including in the area of the second end portion at least two mechanical tape fasteners, the mechanical tape fasteners adapted to be, upon application of the article on the user, detachably interconnected with at least one fastening part disposed on the outer layer of the first end portion and being complementary to said mechanical tape fasteners, wherein the two mechanical tape fasteners are oppositely arranged on the inner layer of the article at opposite side portions of said second end portion, the two mechanical tape fasteners each have one longitudinal and one transverse extension, said mechanical tape fasteners are each permanently joined to the inner layer of the article by means of a producer's bonding face arranged on a first end part of each of the tape fasteners, a user's bonding face is arranged on an opposite second end part of each of the tape fasteners, and wherein prior to use of the article, the tape fasteners are arranged in a folded storage condition in which each one of said tape fasteners is formed with an odd number of folds, both said producer's bonding face and said user's bonding face are turned towards the inner layer of the article, and the second end parts of the two tape fasteners extend toward one another in said storage condition and in the storage condition of said article, each of the tape fasteners includes a first fold part that is joined to at least one other fold part by means of a bond, said bond being breakable in order to secure the user's bonding face to said at least one complementary fastening part upon application of the article, and wherein in their condition of storage, the tape fasteners are arranged in their entirety on the inner layer, with laterally outermost end edges of the tape fasteners being located interiorly of lateral edges of said opposite side portions;

wherein each user's bonding face is in the form of hooks of a hook-and-loop fastener and the at least one complementary fastening part being formed with apertures, loops or fiber filaments for co-operation with the hooks; and wherein the inner layer of the article comprises fibers to which the hooks of each user's bonding face fasten in the storage position to form a bond which is weaker relative to a bond formed by the interconnection of the hooks of each of the user's bonding faces and with said at least one complementary fastener and said breakable bond between the first fold part and the at least one other fold part.

11. The article as claimed in claim 10, wherein the odd number of folds is one fold only and wherein in the folded storage condition the one fold forms the laterally outermost end edge of each tape fasteners, the first fold part forms the second end part, said first end part forms the at least one other fold part, and the opposite second end part is located laterally interiorly of the first end part so as to cover the latter.

12. The article as claimed in claim 10, wherein an outermost end piece of the second end part of each of the mechanical tape fasteners is coated with a pressure-sensitive adhesive providing a weak adhesion force.

13. The article as claimed in claim 10, wherein each breakable bond is designed to ensure that a force in the range of 0.2 to 2N is required to break the bond when the mechanical tape fasteners have a transverse extension of 40 mm.

14. The article as claimed in claim 10, wherein each breakable bond is in the form of a pattern of points or lines, and the bond is breakable without damage to the tape fastener.

15. The article as claimed in claim 10, wherein the mechanical tape fasteners have a width of between 30 and 10 mm.

16. The article as claimed in claim 10, wherein each of the mechanical tape fasteners comprise at least one elastic part disposed between the first end part and the second end part, said elastic part arranged to stretch upon occurrence of load during use of the article.

17. The article as claimed in claim 10, wherein the mechanical tape fasteners do not stretch upon occurrence of load during use of the article.

18. The article as claimed in claim 10, wherein the article is a baby diaper or an incontinence diaper.

19. The article as claimed in claim 10, wherein each breakable bond is designed to ensure that a force in the range of 0.5 to 1.5N is required to break the bond when the mechanical tape fasteners have a transverse extension of 40 mm.

* * * * *